(12) United States Patent
Abolaban

(10) Patent No.: US 11,266,740 B1
(45) Date of Patent: Mar. 8, 2022

(54) NOBLE METAL NANOPARTICLES WITH RADIAL PORES

(71) Applicant: King Abdulaziz University, Jeddah (SA)

(72) Inventor: Fouad Abdulaziz Abolaban, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/012,820

(22) Filed: Sep. 4, 2020

(51) Int. Cl.
| | |
|---|---|
| *A61K 41/00* | (2020.01) |
| *G01N 33/543* | (2006.01) |
| *A61K 33/243* | (2019.01) |
| *A61N 5/10* | (2006.01) |
| *A61K 33/242* | (2019.01) |
| *A61K 9/00* | (2006.01) |
| *B82Y 5/00* | (2011.01) |

(52) U.S. Cl.
CPC ........ *A61K 41/0038* (2013.01); *A61K 33/242* (2019.01); *A61K 33/243* (2019.01); *A61N 5/10* (2013.01); *G01N 33/54346* (2013.01); *A61K 9/0019* (2013.01); *A61N 2005/1085* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 6,355,270 B1 * | 3/2002 | Ferrari | A61P 35/00 424/489 |
| 8,033,977 B2 | 10/2011 | Hainfeld et al. | |
| 9,274,105 B2 | 3/2016 | Guo et al. | |
| 2014/0128408 A1 * | 5/2014 | Kozikowski | A61K 51/0453 514/254.09 |

FOREIGN PATENT DOCUMENTS

| | | |
|---|---|---|
| CN | 108578427 A | 9/2018 |
| JP | 2018083780 A | 5/2018 |
| WO | 2016/191247 A1 | 12/2016 |

OTHER PUBLICATIONS

Du, X., et al., "Dendritic Silica Particles with Center-Radial Pore Channels: Promising Platforms for Catalysis and Biomedical Applications", Small, pp. 392-413 (Year: 2015).*
Fang, J., et al., "A general soft-enveloping strategy in the templating synthesis of mesoporous metal nanostructures", Natunre Communications, pp. 1-9 (Year: 2018).*
Lin, Y., "Impacts of Mesoporous Silica Nanoparticle Size, Pore Ordering, and Pore Integrity on Hemolytic Activity", JACS, pp. 4834-4842 and 1-10, (Year: 2010).*
Hua, W., et al., "Control of pore structure in a porous gold nanoparticle for effective cancer cell damage", Nanotechnology, pp. 1-10 (Year: 2018).*
Ayesha Ihsan, Habib Katsiev, Noktan Alyami, Dalaver H. Anjum, Waheed S. Khan, Irshad Hussain, "From porous gold nanocups to porous nanospheres and solid particles—A new synthetic approach", Journal of Colloid and Interface Science, vol. 446,pp. 59-66, (Year: 2015).*
Setua, S., et al., "Cisplatin-tethered gold nanospheres for multimodal chemo-radiotherapy of glioblastoma" Nanoscale, pp. 10865-10873 (Year: 2014).*
Tao, X., et al., "Effect of pore size and porosity distribution on radiation absorption and thermal performance of porous solar energy absorber", Science China, pp. 2213-2224 (Year: 2019).*
Jana et al., "Self-assembly of Pt(II) based nanoscalar ionic hexagons and their anticancer potencies", Inorganica Chemica Acta, vol. 484, Jan. 1, 2019, pp. 19-26.
Peukert et al., "Nanoparticle optimization for therapy", Med. Phys. 47(2), Feb. 2020, pp. 651-661.
Amato et al., "Gold nanoparticles as a sensitising agent in external beam radiotherapy and brachytherapy: a feasibility study through Monte Carlo simulation", Int. J. Nanotechnol., vol. 10, No. 12, 2013, pp. 1045-1054.

* cited by examiner

*Primary Examiner* — Michael G. Hartley
*Assistant Examiner* — Lance W Rider
(74) *Attorney, Agent, or Firm* — WC&F IP

(57) ABSTRACT

Nanoparticles having radially-oriented pores are fabricated from a noble metal. The pores have a specific geometrical shape, such as a circle, triangle, hexagon or other polygon. The nanoparticles are administered to a subject to form a nanoparticle-loaded tumor, which is targeted with a radiation beam as part of a radiotherapeutic treatment. The pores redirect photons of the radiation beam to intensify and enhance the dose received by tumor cells, while concomitantly reducing the dose received by surrounding cells and/or tissues. The nanoparticles may be combined with a radiosensitizing drug or agent, administered together or separately, to form a dose-enhancement composition that further intensifies the received dose of radiation at the target.

16 Claims, 9 Drawing Sheets

NOBLE METAL NANOPARTICLES WITH RADIAL PORES

BACKGROUND OF THE INVENTION

Field of the Invention

The invention generally relates to nanoparticles, particularly noble metal nanoparticles having radial pores. The invention further relates to uses of nanoparticles in methods using radiotherapy for treating tumors.

Background

One of the leading causes of death worldwide is cancer. Due to a trend towards an aging population, the number of cancer-diagnosed patients is rapidly increasing. Currently, the standard of care for treating cancer is radiotherapy, chemotherapy and surgery, alone or in some combination. Radiotherapy is used in about 50% of cancer treatments. The efficacy of the treatment depends on the deposition of energy directly and accurately into tumor tissue. Dose calculation is one of the principal aspects of radiation therapy treatment planning Energy deposition from single radiation was well defined theoretically decades ago, however, when too many radiation types and energies are present and at different intensities it is challenging to calculate the exact dose delivered with 100% precision (Haume et al., 2016. Cancer Nanotechnol (7)8. doi.org/10.1186/s12645-016-0021-x). In these cases, radiological scientists have used diverse approaches to calculate a proposed dose by putting in all factors that affect the dose distribution. Monte Carlo and speed computers contribute to solving complex and advanced cases and align with significant agreement to theoretical approaches.

Nanotechnology involves manipulation of particles of materials having dimensions typically ranging between 1 nm to 1 µm. By comparison, this range is smaller than human cells and comparable to the size of many proteins and enzymes. Therefore, their use in biological science has enabled probing the cellular structure. There are many types of NP structures, although they can be categorized into three major groups: organic (liposomes and polymers), inorganic (gold, silica, titanium dioxide, quantum dots), and carbon-based. Nanoparticles (NPs) typically are solid and come in colloidal or clustered in different forms.

Nanomedicine is the application of nanotechnology in general healthcare, and particularly concerns the diagnosis and treatment of diseases. especially cancer. In recent years, several fields in the biological and medical sciences, such as molecular biology, imaging, targeted drug delivery, nonviral gene delivery systems and dental implants, have greatly beneficiated from the massive development of nanotechnology. NPs are used in both diagnostic and therapeutic applications. NPs can comprise a core material to encapsulate drugs or contrast agents for imaging and a surface coating to avoid their in vivo phagocytosis or ligand conjugation. Examples of nano-scale structures used in diagnostic and therapeutic applications include quantum dots, nanotubes, nanocages, magnetic NPs, liposomes, nanowires magnetic resonance imaging contrast agents for intraoperative imaging and novel NP-based methods for the highly specific detection of DNA and protein. Due to their considerably large surface-area-to-volume ratio, NPs can be conjugated or otherwise linked to significant amounts of drugs and be dispersed easily throughout the bloodstream.

Nanoparticles (NPs) are used in radiation treatment to increase a dose inside the tumor by increasing the scattered radiation directed back from NPs into the tumor. Thus, NPs can enhance dose distribution by surrounding a tumor while reducing the primary dose to healthy tissues. In some cases, the enhancement benefit reduces the number of treatment fractions needed and/or allows for a greater time interval between treatment fractions for normal cells to recover. By achieving this reduction, treatment fractions can be adapted to reduce the total dose and at the same time the co-incident dose to non-tumorous adjacent cells and organs is reduced. For example, WO2016191247A1 discloses radioactive nanoparticles and a method of performing brachytherapy using the radioactive nanoparticles of 50 to 300 nm in diameter. The radioactive nanoparticles comprise a metallic core, an outer metallic shell, and a metallic radioisotope disposed within either the metallic core or the outer metallic shell. The outer metallic shell may be porous, with a mean pore size of 0.5 to 3 nm, but the pores appear to only be present on hollow nanoparticles. U.S. Pat. No. 8,033,977B2 discloses a method of "enhancing the effects of radiation directed to a tissue of population of cells" comprising administering metal nanoparticles to the tissue and irradiating the tissue. The metal nanoparticles are described as having a size in the range of 0.8 to 400 nm. CN108578427A discloses folic acid-modified, crosslinked gold nanoparticles of about 60 nm in diameter and a method of tumor radiotherapy sensitization using the nanoparticles. The folic-acid modified gold nanoparticles comprise surface ligands of thiol- and amine-containing polyethylene glycol, folic acid, and N-[3-(3-methyl-3H-aziridine-3-yl)propionyloxy]succinimide, a UV-sensitive crosslinking agent. Prior to treatment, the nanoparticles are exposed to UV light, which activates the UV-sensitive crosslinking agent and causes the nanoparticles to exist as clusters or agglomerates held together by covalent bonds between surface ligands. JP2018083780A discloses a porous composite material comprising gold nanoparticles and a bioadsorbable polymer matrix. The composite material generates heat upon exposure to near infrared radiation, said heat being useful in therapeutic methods. Jana, et. al. (*Inorganica Chimica Acta,* 2019. (484):19-26) discusses Pt(II)-based nanoscale hexagonal macrocycles as anticancer agents. The macrocycles contain pyrazine-containing "acceptor" ligands and pyridyl-containing "donor" ligands. The macrocycles have a single hexagonal pore in an overall planar hexagonal shape. Peukert, et. al. (*Med. Phys.,* 2020. (42)2:651) teaches the use of gold nanoparticles of various sizes and with various surface coatings as sensitizing agents for photon beam radiotherapy. The disclosed gold nanoparticles have sizes from 2 to 200 nm and PEG or silica surface coatings of 2 to 20 nm. Amato, et. al. (*Int. J. Nanotechnol.* 2013. (10)12: 1045) teaches the use of gold nanoparticles as sensitizing agents for photon beam radiotherapy.

Many studies in the literature emphasize the usage of different nanoparticles sizes and atoms (Hosyar et al. 2016. *Nanomed* (11):673-692). Ma et al. studied three different shapes of NPs, namely spherical gold nanoparticles (GNPs), gold nanospikes (GNSs), and gold nanorods (GNRs) all at the same size of (~50 nm). Ma found that the sensitization enhancement ratios (SERs) were 1.62, 1.37, and 1.21 corresponding to the treatments of GNPs, GNSs, and GNRs, respectively. However, the GNPs showed higher anticancer efficiency than both GNSs and GNRs (Ma et al. 2017. *ACS Appl. Mater. Interfaces* (9):13037-13048). Zhang et. al. also used gold nanoparticles for in-vitro and in-vivo studies to examine the best radiosensitization size of 4.8, 12.1, 27.3, and 46.6 nm coated gold nanoparticles. Their results show that all sizes of the PEG-coated gold NPs can cause a significant decrease in cancer cell survival however 12.1 and 27.3 nm PEG-coated gold NPs have stronger sensitization effects than 4.8 and 46.6 nm particles (Zhang et al., 2012. *Biomaterials* (33):6401-6419). Hirn et. al. used [198]Au-radio-labelled monodisperse, negatively charged gold NPs of five different sizes 1.4, 5, 18, 80, and 200 nm on rats to study and determine the biodistribution. Hirn found that each gold NPs accumulated in various organs and tissues, which highly depending on NPs size and surface charge (Hirn et al. 2011. *Euro J Pharm Biopharm* (77)"407-416). However, none of them studied the effect of diverse shapes having the same size and the same nanoparticle.

Despite the recent advances in NPs for use in radiation, a need exists for improved methods to enhance the radiation dose delivered to a tumor while minimizing the co-incident dose received by healthy cells and tissues surrounding the tumor.

SUMMARY OF THE INVENTION

An aspect of the invention is a nanoparticle that goes beyond the ranges of size and materials found in the prior art to provide a radiation dose-enhancing substance. Nanoparticles with pores having a defined geometric shape influence the direction of a beam of radiation and provide a mechanism for redirecting a radiation beam passing through a target. The redirection of the beam increases the dose in the target area and decreases the dose of co-incident radiation to surrounding cells and/or tissues.

Another aspect of the invention is porous metal nanoparticle for an antitumor treatment. The nanoparticle is essentially a sphere shape having a plurality of pores arrayed around the outer surface of the sphere. Each pore has a geometric shape that projects outwardly along a radius, beginning near a center-point of the sphere and extending through the surface of the sphere. The geometric shape is one selected from the group consisting of circle, oval triangle, square, rectangle, pentagon, hexagon, a polygon and a parallelogram. The metal is an element selected from the group known as noble metals, which are ruthenium, rhodium, palladium, silver, osmium, iridium, platinum and gold.

In one embodiment, the spherical nanoparticle has a diameter of 1 µm. The plurality of pores typically are present in the range of 60 to 100 pores, but can have fewer or more pores outside this range. The volume of the pores can be expressed as a proportion of the total volume of the sphere, in the range of approximately 3 to 5%. Alternatively, the amount of space on the surface can be used to show pore volume. For example, when the nanoparticle has a surface area in the range of $1.25\times10^{-21}$ to $4.50\times10^{-21}$ m$^2$ per particle, the plurality of pores may have a total volume in the range of $0.625\times10^{-24}$ to $2.25\times10^{-24}$ m$^3$ per particle.

In another embodiment, the invention is a method of treating a tumor in a subject in need thereof, comprising the steps of providing a dose-enhancement substance or composition comprising porous noble metal nanoparticles, delivering a suitable quantity of the dose-enhancement substance to at least one tumor in the subject to form at least one nanoparticle-loaded tumor, and administering to the subject a radiological treatment. The radiological treatment typically comprises directing a beam of radiation to the nanoparticle-loaded tumor, whereupon the porous noble metal nanoparticles intensify the dose applied to the nanoparticle-loaded tumor. This occurs due to the beam hitting the pores of the nanoparticle and redirecting the beam of radiation away from surrounding tissues and into cells of the nanoparticle-loaded tumor. Thus, the method of treatment provides at least two benefits: 1) redirecting radiation away from surrounding cells and tissues and 2) redirecting radiation to the tumor cells, thereby enhancing the dose provided by the radiological treatment. This reduction of dose can be a change in treatment fraction or a decreased interval between treatments.

In one embodiment, the method provides a radiation dose-enhancement by a factor of 1.01 to 1.5 compared to a radiation dose to a tumor in the absence of the dose-enhancement substance comprising porous noble metal nanoparticles.

In another embodiment, the method provides a radiation dose-enhancement by a factor of 1.01 to 1.10 compared to a radiation dose to a tumor in the absence of the dose-enhancement substance comprising porous noble metal nanoparticles. In yet another embodiment, the method provides a radiation dose-enhancement by a factor of at least 1.01.

In yet another embodiment, a dose-enhancement composition comprises porous noble metal nanoparticles and at least one radio-sensitizing drug or agent. Radiosensitizing drugs and agents are known in the art and enhance tumor cell sensitivity by altering or dysregulating cell cycle checkpoints, inhibiting DNA repair, or causing or aggravating DNA damage or misrepair mechanisms. Other radiosensitizing agents increase oxygen in tumors and increase the effectiveness of a dose of radiation by forming DNA-damaging free radicals. Other radiosensitizing drugs and agents are also suitable, and are not limited to the mechanisms listed here.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 1A shows a sphere having circular air cavities (CS). FIG. 1B shows a sphere having hexagonal air cavities (HS). FIG. 1C shows a sphere having triangular air cavities (TS) and FIG. 1D shows a cross-sectional view of the TS.

FIG. 2A shows a 2D drawing of a cross-section of a CS nanoparticle. FIG. 2B shows diameter A, which is equal to 1 µm, and a pore opening of 0.05 µm of a CS nanoparticle FIG. 2C shows a quarter cut-away cross-sectional view of a three-dimensional CS nanoparticle. FIG. 2D shows the taken portion of the CS nanoparticle to represent FIG. 2C. FIG. 2E shows a three-dimensional view of a CS nanoparticle. FIG. 2F shows a three-dimensional side view of a CS nanoparticle cut along a diameter.

FIGS. 3A and 3B are three-dimensional views of the arrangement of nanoparticles within the water phantom. FIG. 3C is a top view and FIG.

3D is a front view showing a two-dimensional arrangement of nanoparticles within the water phantom. Elements of the figures are not drawn to scale.

Figure 4:
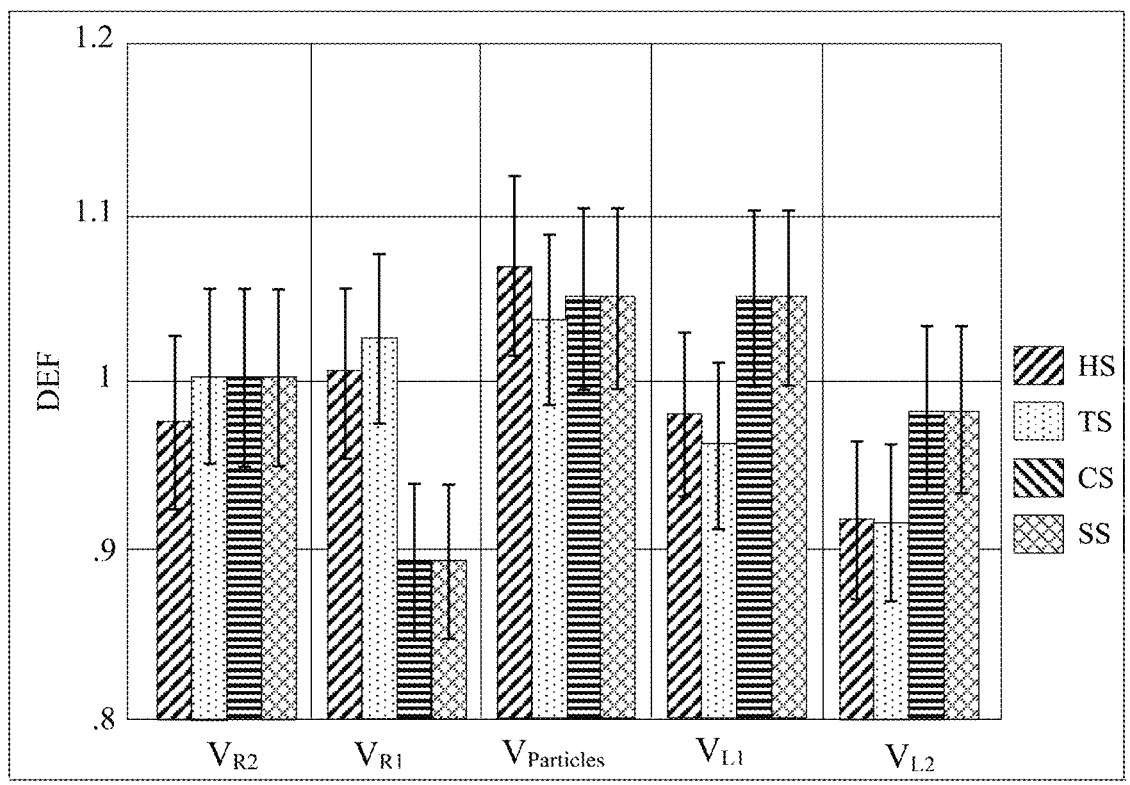

FIG. 4 shows the transverse dose enhancement profile for primary radiation using gold microparticles. $V_{particle}$: central voxel, $V_{L1}$: first left voxel, $V_{L2}$: second left voxel, $V_{R1}$: first right voxel and $V_{R2}$: second right voxel.

Figure 5:
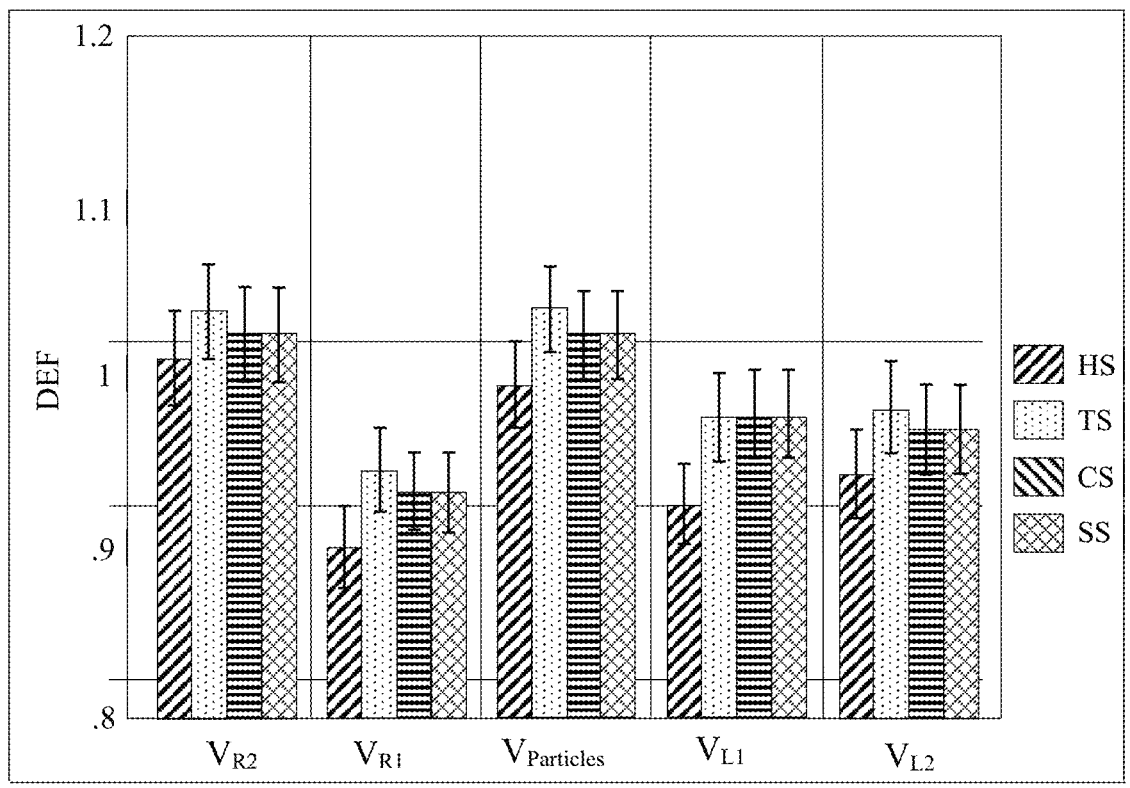

FIG. 5 shows the transverse dose enhancement profile for secondary radiation using gold microparticles. $V_{particle}$: central voxel, $V_{L1}$: first left voxel, $V_{L2}$: second left voxel, $V_{R1}$: first right voxel and $V_{R2}$: second right voxel.

Figure 6:
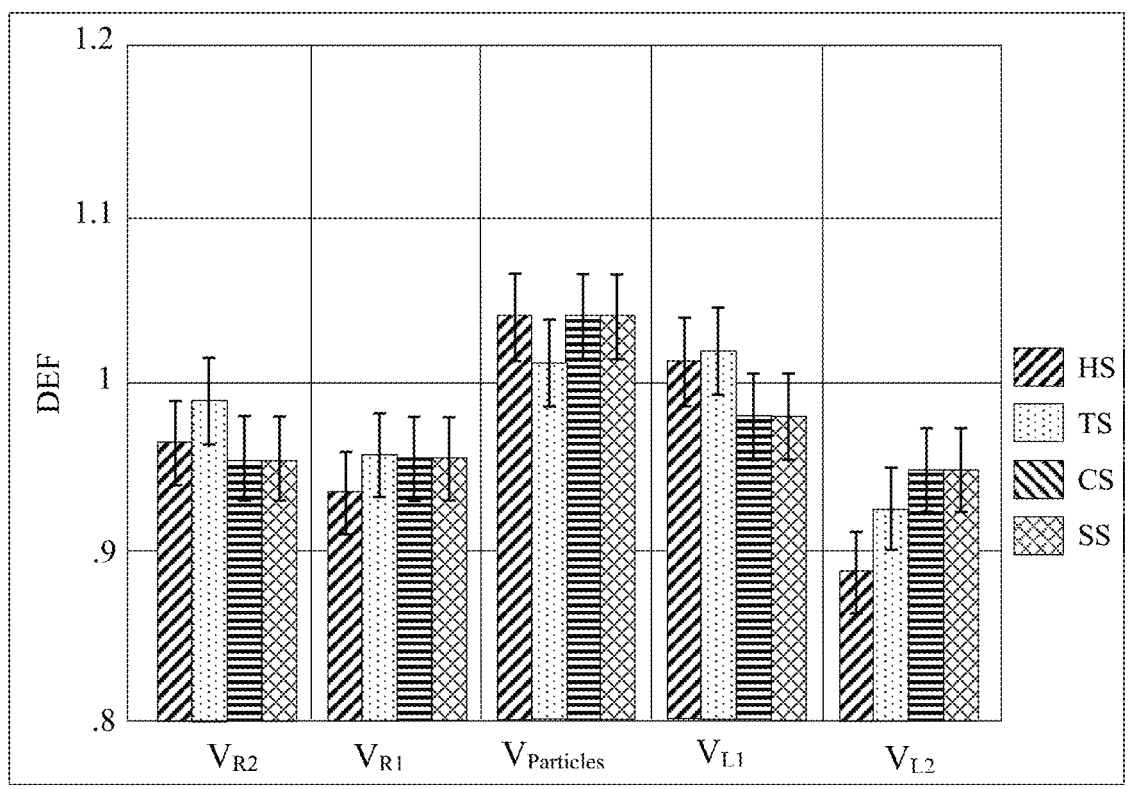

FIG. 6 shows the transverse dose enhancement profile for total radiation using gold microparticles. $V_{particle}$: central voxel, $V_{L1}$: first left voxel, $V_{L2}$: second left voxel, $V_{R1}$: first right voxel and $V_{R2}$: second right voxel.

Figure 7:
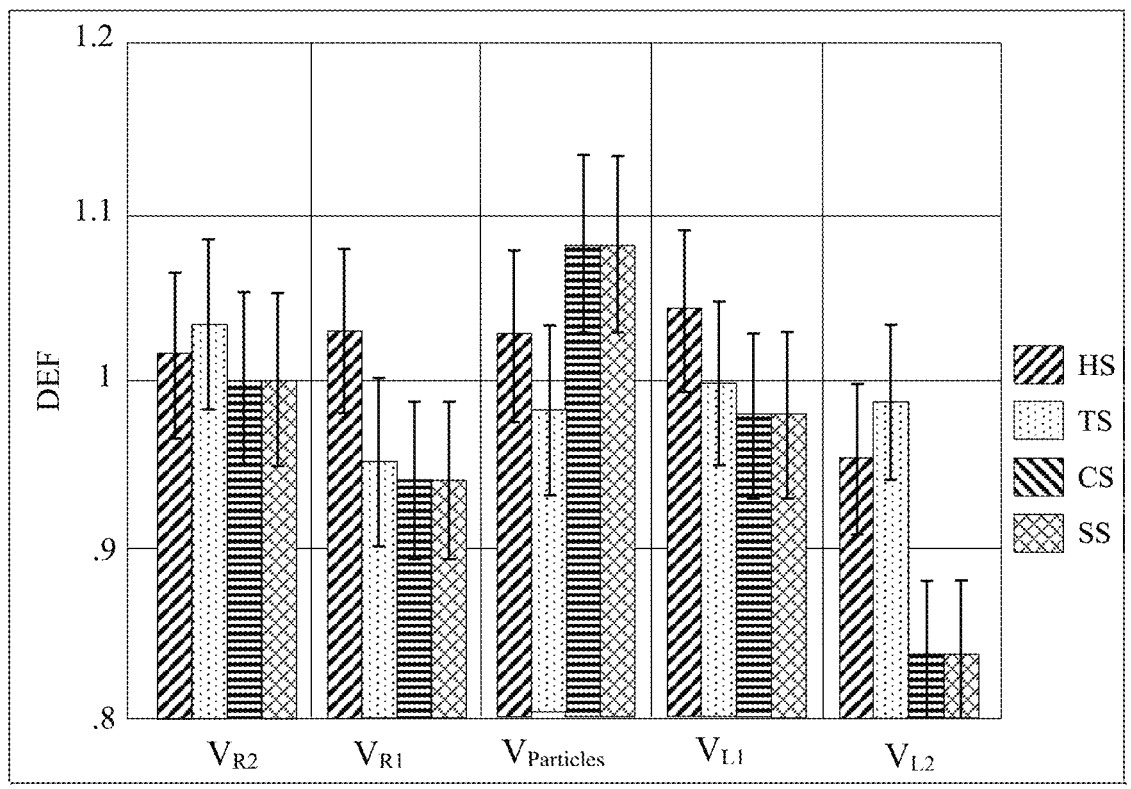

FIG. 7 shows the transverse dose enhancement profile for primary radiation using platinum microparticles. $V_{particle}$: central voxel, $V_{L1}$: first left voxel, $V_{L2}$: second left voxel, $V_{R1}$: first right voxel and $V_{R2}$: second right voxel.

Figure 8:
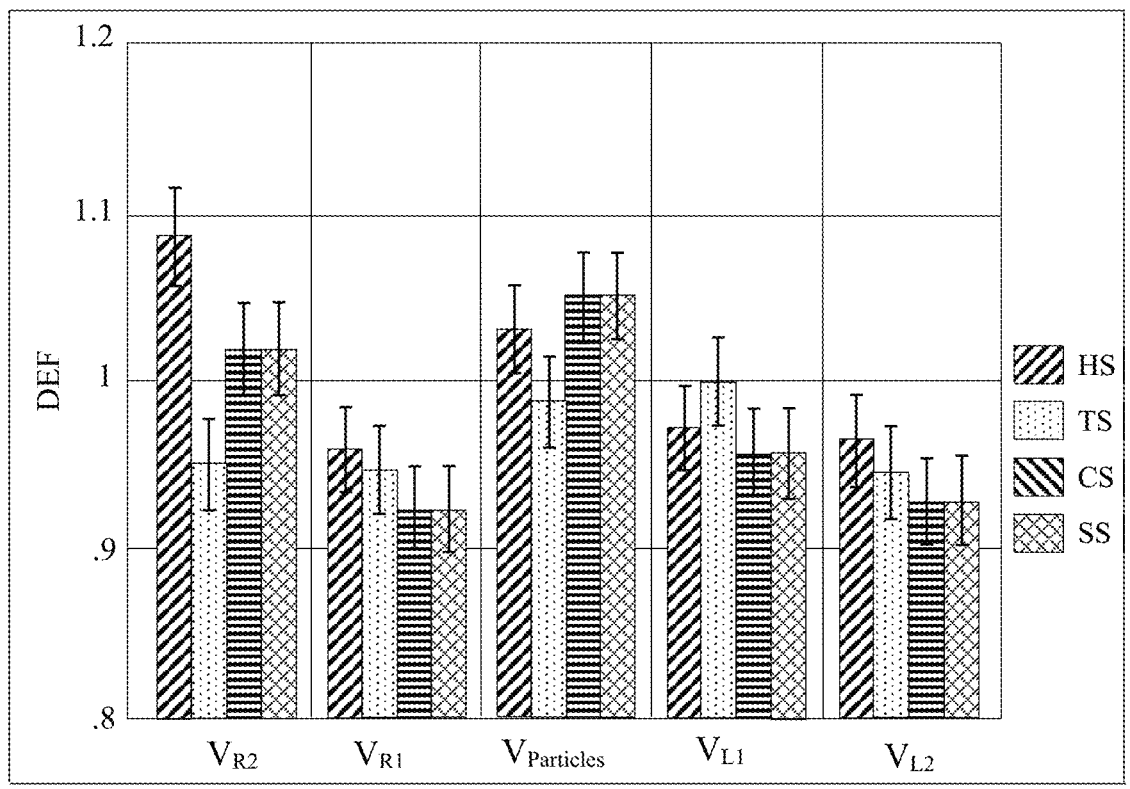

FIG. 8 shows the transverse dose enhancement profile for secondary radiation using platinum microparticles. $V_{particle}$: central voxel, $V_{L1}$: first left voxel, $V_{L2}$: second left voxel, $V_{R1}$: first right voxel and $V_{R2}$: second right voxel.

Figure 9:
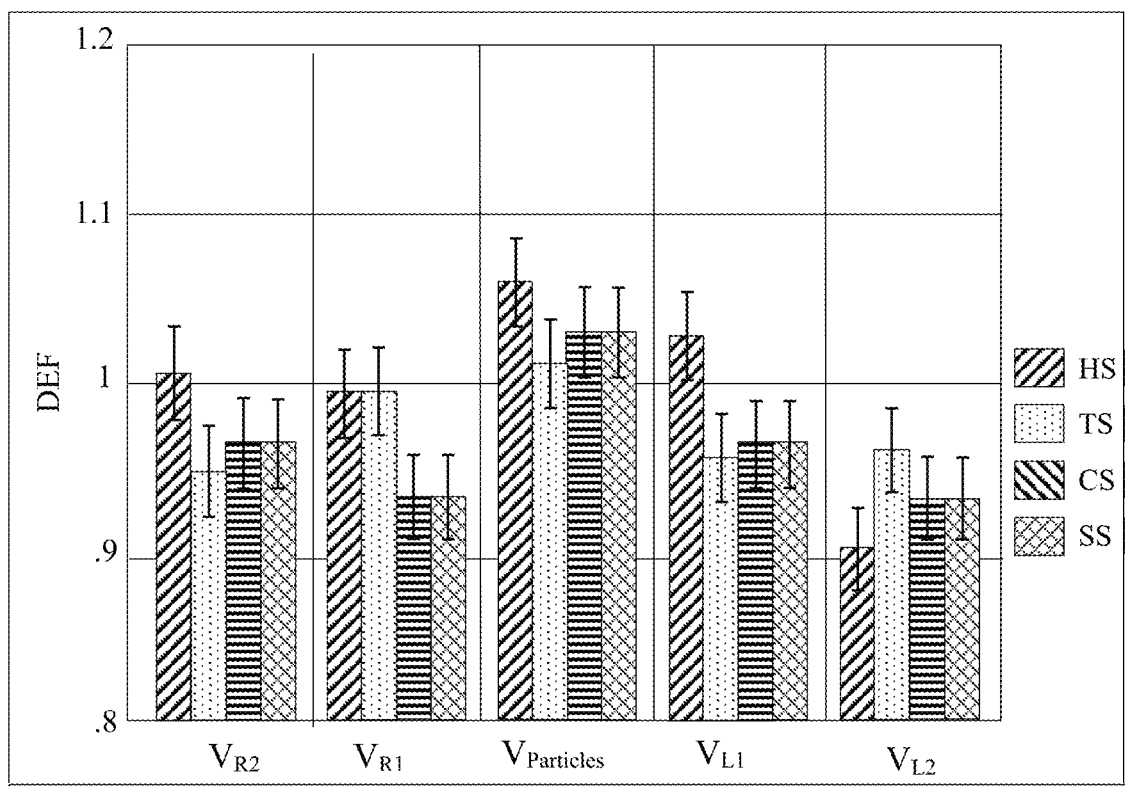

FIG. 9 shows the transverse dose enhancement profile for total radiation using platinum microparticles. $V_{particle}$: central voxel, $V_{L1}$: first left voxel, $V_{L2}$: second left voxel, $V_{R1}$: first right voxel and $V_{R2}$: second right voxel.

DETAILED DESCRIPTION

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

An important aspect of the invention is providing a nanoparticle with pores having a defined geometric shape to enhance a radiological treatment. The shape of the pore influences the direction of a beam of radiation and provides a mechanism for redirecting a radiation beam as it passes through a targeted tumor.

Treatments are another important aspect of the invention. Subjects are administered nanoparticles of the invention in conjunction with a radiotherapeutic procedure or treatment. When used in the method of the invention, the nanoparticles redirect a radiation beam during a radiotherapeutic treatment and increase the dose in the target area while simultaneously decreasing the dose of co-incident radiation to surrounding cells and/or tissues. The nanoparticles may be combined with a radiosensitizing drug or agent, administered together or separately, to form a dose-enhancement composition that further intensifies the received dose of radiation at the target.

In one embodiment, the invention is porous metal nanoparticle for an antitumor treatment. The nanoparticle is essentially a sphere shape and has a plurality of pores arrayed around the outer surface of the sphere. Each pore has a geometric shape that projects outwardly along a radius, beginning near a center-point and extending through the surface of the porous metal nanoparticle. The geometric shape is selected from the group consisting of circle, oval triangle, square, rectangle, pentagon, hexagon, a polygon and a parallelogram. In one embodiment, the geometric shape is one having corners and the corners increase the redirection of the radiation beam. In another embodiment, the geometric shape is a hexagon. The metal is an element from the group known as noble metals, which are ruthenium, rhodium, palladium, silver, osmium, iridium, platinum and gold. The essentially spherical nanoparticle typically has a diameter 1 μm. The plurality of pores typically are present in the range of 60 to 100 pores, but can have fewer or more pores outside this range. When the nanoparticle has a surface area in the range of $1.25 \times 10^{-21}$ to $4.50 \times 10^{-21}$ m² per particle, the plurality of pores may have a total volume in the range of $0.625 \times 10^{-24}$ to $2.25 \times 10^{-24}$ m³ per particle.

The volume of each air cavity is the multiplication of the radius of the sphere $\theta_R$ by the surface area of the shape. The total volume of the air cavity in each sphere can be calculated using the following equations:

$$\text{Total Air cavity } volum \ (CS) = \sum_{i=0}^{n} \left[ \frac{1}{3} \cdot \pi \cdot r^2 \right] \cdot R \quad (1)$$

$$\text{Total Air cavity } volum \ (TS) = \sum_{i=0}^{n} \left[ \frac{1}{3} \cdot \frac{a \cdot \sqrt{3}}{4} \right] \cdot R \quad (2)$$

$$\text{Total Air cavity } volum \ (HS) = \sum_{i=0}^{n} \left[ \frac{1}{3} \cdot \frac{6 \cdot s^2}{4 \cdot \tan(\frac{\pi}{6})} \right] \cdot R \quad (3)$$

where r is the radius of the circle at the surface of the sphere and R is the radius of the sphere which has a constant value of 0.5 μm for all spheres and shapes; a is the triangular side and s is the hexagonal side and n is the number of cavities in each sphere volume.

In another embodiment, the invention is a method of treating a tumor in a subject in need thereof, comprising the steps of providing a dose enhancement substance comprising porous noble metal nanoparticles, delivering a suitable quantity of the dose enhancement substance to at least one tumor in the subject to form at least one nanoparticle-loaded tumor, and administering to the subject a radiological treatment. The radiological treatment typically comprises directing a beam of radiation to the nanoparticle-loaded tumor, whereupon the pores of the nanoparticles intensify the dose applied to the nanoparticle-loaded tumor. This occurs due to the beam hitting the pores and redirecting the beam of radiation into cells of the nanoparticle-loaded tumor, with the concomitant benefit of decreasing the dose received by the surrounding cells and/or tissues.

The method of the invention provides at least the following two benefits: 1) redirecting radiation away from surrounding cells and tissues that are healthy and 2) redirecting radiation to the tumor cells, thereby enhancing the dose provided by the radiological treatment. A further benefit is that by reducing the dose to healthy tissues, the treatment fraction can be adjusted to a lower dose of radiation energy and/or the recovery time for healthy tissue repair between treatments can be reduced. One of ordinary skill in the art can appreciate that shortening the interval between treatment fractions will increase the pressure on tumor cells, thus increasing the efficacy of the radiation treatment.

In one embodiment, the method provides a radiation dose-enhancement by a factor of 1.01 to 1.5 compared to a radiation dose to a tumor in the absence of the dose-enhancement composition comprising porous noble metal nanoparticles. In another embodiment, the method provides a radiation dose-enhancement by a factor of 1.01 to 1.10 compared to a radiation dose to a tumor in the absence of the dose-enhancement composition comprising porous noble metal nanoparticles. In yet another embodiment, the method provides a radiation dose-enhancement by a factor of at least 1.01.

As used herein, the terms "pores" and "air cavities" are used interchangeably to refer the geometrical holes that are formed in the nanoparticle spheres. The pores or air cavities are arranged as radials, thus the arrangement of the pores may be identified as radially-oriented. The total number of pores is determined by surface area of the shape (i.e. CS, TS, and HS), and is typically in the range of 60 to 100 per sphere. The pore is widest at its opening on the outer surface of a sphere, and progressively narrows along a radius to a termination point within the pore, but does not reach to the center of the sphere, i.e., opposite radials do not meet to form a hole or tunnel that would be a diameter.

As used herein, the term "dose-enhancement" or "dose-enhancing" are used interchangeably to refer to the effect or activity of the composition of porous metal nanoparticles. In some embodiments, the dose-enhancement composition or substance further comprises a pharmaceutical carrier. In other embodiments, the dose-enhancement composition further comprises a radiosensitizing drug or agent.

As used herein, the term "dose-enhancement factor", "dose enhancing factor" or "DEF" is determined by comparing the dose received without nanoparticles to the dose received with nanoparticle. In some embodiments, the DEF is a comparison of the dose received without the dose-enhancement composition and the dose received with the dose-enhancement composition.

As used herein, the term "dose-enhancement composition" or dose-enhancing composition" refers to any combination of nanoparticles with or without one or more sensitizing drug(s), sensitizing agents(s) and/or pharmaceutically acceptable carriers. In some embodiments, the dose-enhancement composition refers to nanoparticles alone.

An objective of the invention is to provide air cavity shapes to the spherical nanoparticles that are used for enhancing a dose of radiation. The pore shapes used for a dose enhancement can be an important aspect and guidance for the design of nanostructures in cancer radiotherapy. Since the energy of a beam of radiation can vary between protocols for various tissues, tumor types, and density or depth of a target area, the air cavity shapes can be pair with a radiation energy to provide an optimized treatment. For example, some shapes can be matched with a particular beam energy to increase or decrease the intensity of redirection. The size, location, depth of tissue and cell type of a target tumor can also be considered when choosing parameters for pore shape, nanoparticle size, number of nanoparticles loaded into a tumor, as well as the parameters for the radiation.

The nanoparticle may be fabricated using any appropriate technique, including some techniques that are well-known in the art. For many applications of metal nanoparticles, an exact knowledge of two main methods is necessary. The bottom-up method, which starts by building up atom by atom, and the top-down method, which takes a material and makes particles of the material smaller and smaller until they are in the nanoparticle size range. Therefore, a special nanoparticle machine that has the ability to design and contour is needed for the fabrication of metal nanoparticles of the invention with properties tailored in size and shape. These machines are well-known in the art.

In one embodiment, a radiosensitizing agent or drug is added to the nanoparticles to form a dose enhancing composition. Conventional chemotherapeutics are currently being used in conjunction with radiation therapy to increase its effectiveness. Examples include the fluoropyrimidines, gemcitabine and platinum analogs; fluoropyrimidines increase sensitivity by dysregulating S-phase cell cycle checkpoints in tumor cells. Gemcitabine progresses through a similar mechanism, causing cells in the S-phase to disrepair DNA damage caused by the radiation. Platinum analogs such as cisplatin inhibit DNA repair by cross linking strands, and so aggravate the effects of DNA damage induced by radiation. Thus, the dose enhancing composition may comprise any of these agents and thereby further increase the effective dose of radiation above the enhancement provided by the nanoparticles. One of the major limitations of conventional radiotherapy is that the cells of solid tumors become deficient in oxygen. This typically occurs when solid tumors outgrow their blood supply, causing a low-oxygen state known as hypoxia. Oxygen is a potent radiosensitizer, increasing the effectiveness of a given dose of radiation by forming DNA-damaging free radicals. Tumor cells in a hypoxic environment may be as much as 2 to 3 times more resistant to radiation damage than those in a normal oxygen environment. Thus, the dose enhancing composition can comprise hypoxic cell radiosensitizers such as misonidazole and metronidazole, or hypoxic cytotoxins, such as tirapazamine Oxygen can also be increased by supplying inhaled oxygen to the patient. This listing is not limiting since other radiosensitizers are known in the art and these would also be suitable for use.

In some embodiments, the porous metal nanoparticles and the radiosensitizing drug(s) or agent(s) may be administered separately, concurrently by different routes, or sequentially to the subject. For example, the nanoparticles may be injected directly into a tumor, and oxygen levels may be increased by increasing inhalation of oxygen by the subject. In another example, the nanoparticles may be coated with a ligand that promotes uptake of the nanoparticles by a tumor, and a radiosensitizer may be administered by intravenous injection. Any combination of suitable administration by injection, inhalation, or other routes is contemplated, and can be tailored to the most appropriate methods for each drug/agent and will also take into account the formulation of the drug/agent. Routes of administration are generally classified by the location at which the substance is applied. Common examples include oral and intravenous administration. Routes can also be classified based on where the target of action is. Action may be topical (local), enteral (system-wide effect, but delivered through the gastrointestinal tract), or parenteral (systemic action, but delivered by routes other than the GI tract).

The method of the invention should also be adapted to the route most appropriate for the target tumor. One of ordinary skill in the art would recognize that tumor location, depth, superficiality, cell type and many other factors would need to be considered. The amount of nanoparticles used to load a tumor or tumors will also depend upon many factors, including tumor burden, radiation target area, the size of any individual tumor to be treated, and the tissue density or cell type of the tumor. Thus, a sufficient number or quantity of nanoparticles will vary depending upon an individual's treatment plan, but in any case, the number or quantity will need to be sufficient for providing a therapeutic effect. In this case, the therapeutic effect can be measured by the DEF that may be calculated based on standard practices and taking into account the redirective potential of the geometric shape of pores on a selected nanoparticle. This can be determined theoretically and by Monte Carlo simulation, as will be shown in the Examples of the invention.

Before exemplary embodiments of the present invention are described in greater detail, it is to be understood that this invention is not limited to any particular embodiments described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following Examples provide exemplary designs and methods for fabricating and using microgrippers of the invention. These Examples describe materials and methods for using embodiments illustrated in FIGS. 1-9. Additional details can be found in the section entitled "Brief Description of the Drawings".

Example 1

Porous Noble Metal Nanoparticles

Accuracy and flexibility of the geometric representation of the nanoparticles were critical factors in choosing a simulation toolkit to characterize the shapes, since the shapes of the nanoparticles of the invention have a somewhat complicated geometry. The software program known as GATE 8.2 (GATE; online at the website found at opengatecollaboration.org) is one of the prominent Monte Carlo simulation toolkits with a wide range of medical physics applications. Furthermore, GATE offers the capability of importing 3D computer-aided design models. Nanoparticles for examples of the invention are generated using SolidWorks® software (Dassault Systemes SolidWorks Corporation; Waltham Mass.), which later were imbedded into GATE. Thus, complex shapes can be modeled more easily in simulation and with acceptable detail.

Figure 1A:
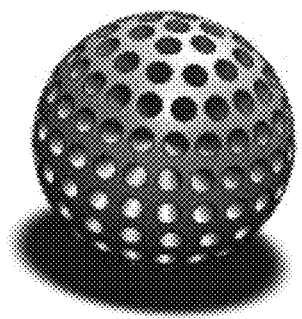
FIG. 1A-1D shows exemplary nanoparticles.
Figure 1B:
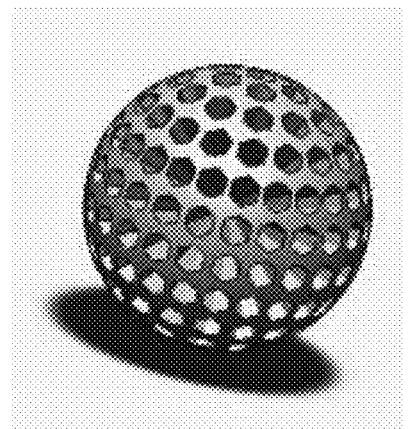
Figure 1C:
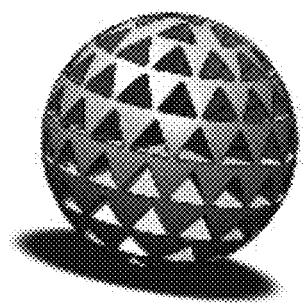
Figure 1D:
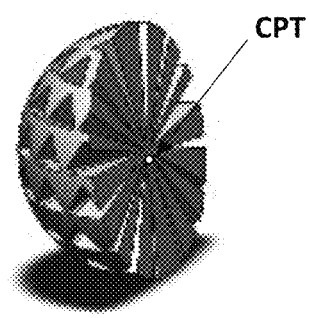

FIG. 1A-1D shows CAD drawings of three configurations of pore shapes or air cavities among those generated using the SolidWorks® software. FIG. 1A shows a sphere having circular air cavities (CS). FIG. 1B shows a sphere having hexagonal air cavities (HS). FIG. 1C shows a sphere having triangular air cavities (TS) and FIG. 1D shows a cross-sectional view of the TS. The invention is not limited to the shapes illustrated in FIG. 1, since one of ordinary skill in the art would recognize that many geometric shapes could be used to produce differing results. The sphere size for all spheres as illustrated is 1 all spheres have a diameter of 1 µm. Thus, the only variable between spheres is the presence or absence of pores and pore shapes.

Figures 2A, 2B, 2C, 2D, 2E, 2F:
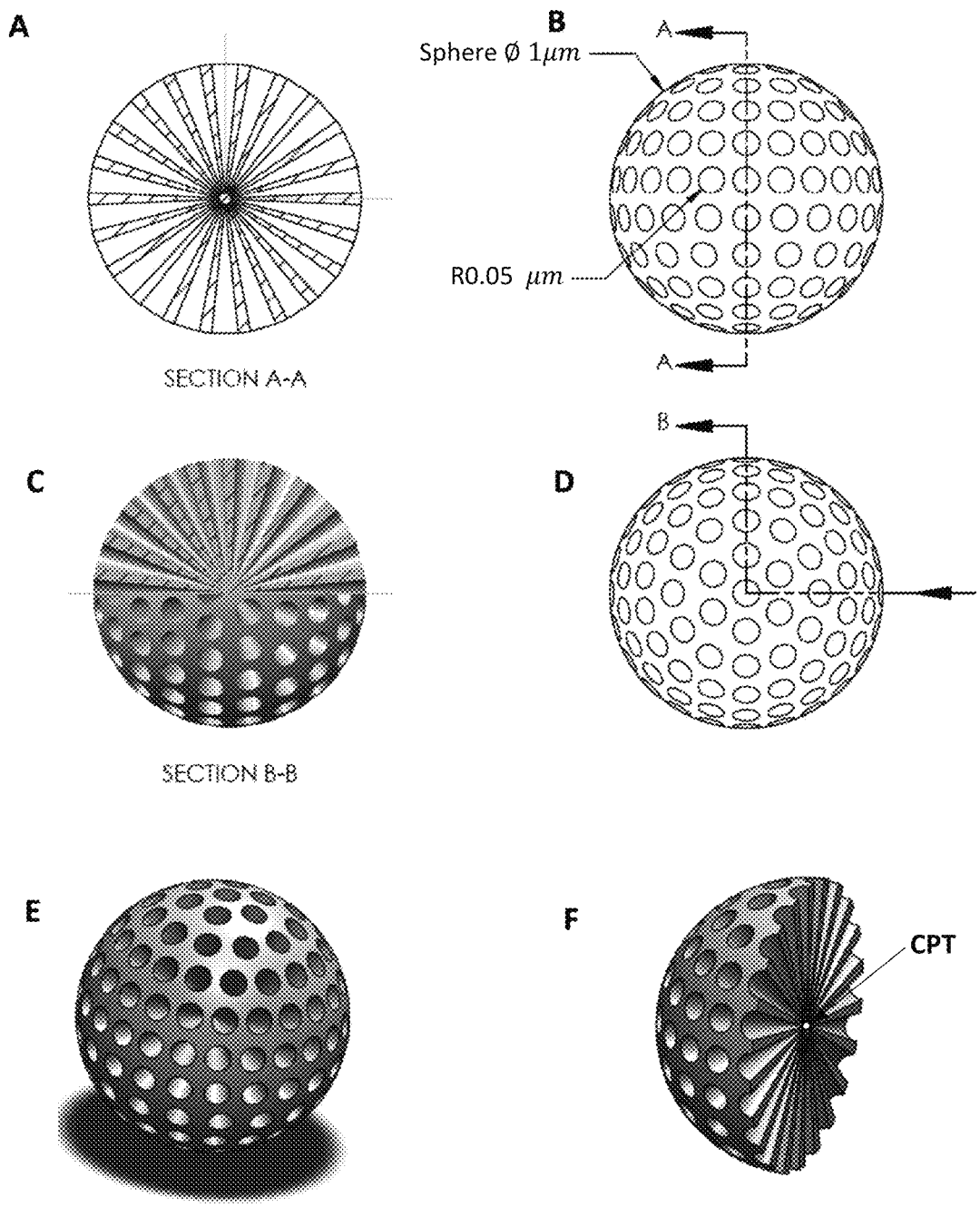
FIGS. 2A-2F shows a series of views of a CS nanoparticle.

FIGS. 2A-2F show various views of one CS nanoparticle and provide dimensional measurements that are exemplary of the radius, diameter and pores of the nanoparticles in this example. FIG. 2A shows a two-dimensional drawing of a cross-section of a CS nanoparticle. FIG. 2B shows diameter A, which is equal to 1 µm, and a pore opening of 0.05 µm of a CS nanoparticle FIG. 2C shows a quarter cut-away cross-sectional view of a CS nanoparticle. FIG. 2D shows the taken portion of the CS nanoparticle to represent FIG. 2C. FIG. 2E shows a three-dimensional view of a CS nanoparticle. FIG. 2F shows a three-dimensional side view of a CS nanoparticle cut along a diameter.

In this example, the radius of the sphere is 0.5 µm. The surface area of HS, TS and CS are ($4.332 \times 10^{-21}$ m$^2$), ($2.892 \times 10^{-21}$ m$^2$) and ($1.312 \times 10^{-21}$ m$^2$), respectively. The volume of each air cavity is the multiplication of the radius of the sphere $\theta_R$ by the surface area of the shape. The total volume of the air cavity in each sphere can be calculated using the following equations:

$$\text{Total Air cavity } volum \ (CS) = \sum_{i=0}^{n} \left[ \frac{1}{3} \cdot \pi \cdot r^2 \right] \cdot R \quad (1)$$

$$\text{Total Air cavity } volum \ (TS) = \sum_{i=0}^{n} \left[ \frac{1}{3} \cdot \frac{a \cdot \sqrt{3}}{4} \right] \cdot R \quad (2)$$

$$\text{Total Air cavity } volum \ (HS) = \sum_{i=0}^{n} \left[ \frac{1}{3} \cdot \frac{6 \cdot s^2}{4 \cdot \tan(\frac{\pi}{6})} \right] \cdot R \quad (3)$$

where r is the radius of the circle at the surface of the sphere and R is the radius of the sphere which has a constant value of 0.5 µm for all spheres and shapes; a is the triangular side and s is the hexagonal side and n is the number of cavities in each sphere volume.

Example 2

Modeling Dose Enhancement of a Radiation Beam

A linear accelerator, VERSA HD linear accelerator, was modeled in simulation in an earlier study where the simulated dose distributions showed a good agreement with the experimental dose distributions. Dose depth distribution and dose profiles were carried out at three different field sizes 10×10, 20×20, and 30×30 cm2. The calculated TPR20,10 for the simulated data was found to be 0.658, 1.1% less than the measured TPR20,10 which was found to be 0.666. The obtained results indicate good agreement between the simulated and measured data, where Gamma Index 3%/3 mm criteria reached values of 97% and 90% for relative dose and dose profiles, respectively.

Figures 3A, 3B, 3C, 3D:
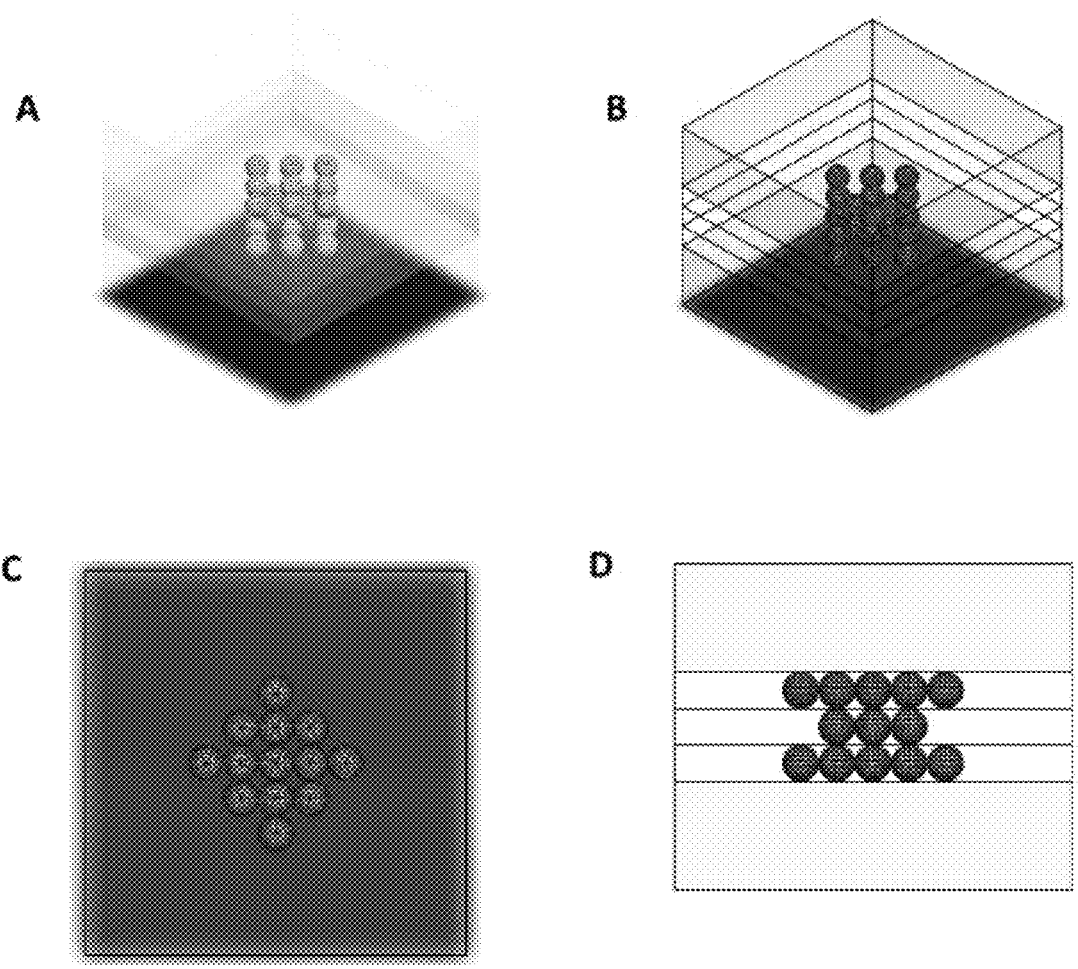
FIGS. 3A-3D shows a theoretical arrangement of nanoparticles stacked in water phantom for a simulation of radiation dose enhancement.

To calculate the dose distribution, a "Dose ACTOR" tool is attached to the phantom. Actors are tools in Gate that collect information of interest in the volume they are attached to (Jan et al., 2011). Using the dose actor, the phantom is split into 1×1×1 mm$^3$ dose calculating voxels. Nanoparticles, such as those in Example 1 shown in FIG. 1, are arranged at the center of the water phantom. FIGS. 3A and 3B are three-dimensional views of the arrangement of nanoparticles within the water phantom. FIG. 3C is a top view and FIG. 3D is a front view showing a two-dimensional arrangement of nanoparticles within the water phantom. The sphere diameter for all 4 spheres is 1 µm. The spacing between the particles in the arrangement is 1 µm in both the x- and y-directions.

Two types of materials were tested in this example: gold ($^{197}$Au) and platinum ($^{195}$Pt). The pore shapes of nanoparticles are hexagonal air cavities sphere (HS), triangular air cavities sphere (TS), circular air cavities sphere (CS), or solid sphere with no air cavities (SS). The pore shapes are the same as those in Example 1, as illustrated in FIG. 1, except that SS is not shown in FIG. 1. Thus, the variables are a) gold or platinum material, and b) the presence or absence of pores, and c) pore shapes.

Tumor mass as a voxel of 1 mm inside a water phantom of 5×5×5 cm$^3$ is exposed to 6MV photon beam. This voxel contains 17 identical nanoparticles stacked together as shown in FIGS. 2A-2D, which illustrate theoretical diagrams of nanoparticles stacked in a water phantom.

The beam is generated by VERSA HD linear accelerator Monte Carlo simulation. Dose distribution at all adjacent voxel is measured using a "DOSE ACTOR" tool available in GATE 8.2 simulation code.

The results are presented as dose enhancement factor (Dose Enhancement Factor, DEF) and focused on the dose inside the centered voxel that contains the nanoparticles as well as adjacent voxels. As mentioned above, each voxel is 1 mm$^3$ and the results are all shown per voxel.

FIGS. 4-9 shows the primary, secondary and total radiation dose at five voxels for gold and platinum porous nanoparticles. The center voxel named $V_{particle}$ were the first two left side voxels from $V_{particle}$; identified as $V_{L1}$ and $V_{L2}$. Similarly for $V_{R1}$ and $V_{R2}$, the first two right-side voxels are from $V_{particle}$.

The DEFs values for the $^{197}$Au at $V_{particle}$ are 1.0402, 1.0131, 1.0412 and 1.0412 for HS, TS, CS, and SS respectively. The highest DEF for the $^{197}$Au nanoparticles is received by CS and SS.

The DEFs values for the $^{195}$Pt at $V_{particle}$ are 1.0583, 1.0110, 1.0291 and 1.0292 for HS, TS, CS and SS respectively. The highest DEF for $^{195}$Pt is received by HS.

Variation of the results among the different shapes that the dependence of the nanoparticles is dependent on the types and shapes and also on the surface compositions of the particles. Without being bound by theory, the six edges of the HS surface entrances appear to increase radiation scatter and produce more radiation and energy deposition inside the cavities that hold the tumor cells.

The objective of this example is to demonstrate the effect of changing the surface interaction of the same nanoparticles. Surface interaction of the added dose-enhancing nanoparticles would affect the absorbed dose and increase the DEF by a factor of at least 1.05 in the case of HS.

In some embodiments, the DEF is in the range of 1.01 to 1.5.00, while others were in the range of 1.02 to 1.40, 1.03 to 1.50, 1.04 to 1.40 or 1.05 to 1.20.

There are four surface shapes in this study. The main difference among these shapes is the air cavity which leads to the amount that the tumor cells can accommodate in these volumes. The air cavity volume of the HS is 2.166×10$^{-27}$ m$^3$ which makes the maximum DEF in this example. It can be seen from FIGS. 4-9 there is no scattering effect on adjacent voxels. However, in high treatment energy such as 10, 15 and 18 MeV these results may vary accordingly. Thus, the air cavity shape and treatment energy can be designed as a paired treatment to deliver an optimized DEF. Other shapes are contemplated and may be used in combinations of various treatment energies.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A dose-enhancement composition for an antitumor treatment, comprising a spherical metal nanoparticle having a substantially spherical shape that has a center-point and having a plurality of geometrical holes, wherein
   each geometrical hole has a cross-sectional hexagonal shape and projects outward radially, beginning at a hole termination point that is near the center-point and extending to a hexagonal opening at an outer surface of the spherical metal nanoparticle, and
   the metal is selected from the group consisting of ruthenium, rhodium, palladium, silver, osmium, iridium, platinum, and gold.

2. The dose-enhancement composition of claim 1, wherein the spherical metal nanoparticle has a diameter in the range of 0.5 to 1 microns.

3. The dose-enhancement composition of claim 1, wherein the plurality of geometrical holes that are present is in the range of 60 to 100 geometrical holes.

4. The dose-enhancement composition of claim 1, wherein the plurality of geometrical holes has a total volume in the range of 0.625×10-24 to 2.25×10-24 m3 per spherical metal nanoparticle.

5. The dose-enhancement composition of claim 1, further comprising a radiosensitizing drug or agent.

6. The dose-enhancement composition of claim 1, further comprising a pharmaceutically acceptable carrier.

7. A dose-enhancement composition for an antitumor treatment, comprising:

a spherical metal nanoparticle having a substantially spherical shape that has a center-point and having a plurality of geometrical holes, wherein each geometrical hole has a cross-sectional shape and projects outward radially, beginning at a hole termination point that is near the center-point and extending to an opening at an outer surface of the spherical metal nanoparticle, wherein the metal is selected from the group consisting of ruthenium, rhodium, palladium, silver, osmium, iridium, platinum, and gold; and a radiosensitizing drug or agent positioned within said plurality of geometrical holes.

8. The dose-enhancement composition of claim 7, wherein the spherical metal nanoparticle has a diameter in the range of 0.5 to 1 microns.

9. The dose-enhancement composition of claim 7, wherein the plurality of geometrical holes that are present is in the range of 60 to 100 geometrical holes.

10. The dose-enhancement composition of claim 7, wherein the plurality of geometrical holes has a total volume in the range of $0.625 \times 10^{-24}$ to $2.25 \times 10^{-24}$ m3 per particle.

11. The dose-enhancement composition of claim 7, further comprising a pharmaceutically acceptable carrier.

12. The dose-enhancement composition of claim 7, wherein the cross-sectional shape of the plurality of geometrical holes is hexagonal.

13. The dose-enhancement composition of claim 7, wherein the radiosensitizing drug or agent is selected from the group consisting of fluoropyrimidines, gemcitabine, and platinum analogs.

14. The dose-enhancement composition of claim 1 wherein the metal is platinum or gold.

15. The dose-enhancement composition of claim 1, further comprising each geometrical hole progressively narrowing from the hexagonal opening to the hole termination point.

16. The dose-enhancement composition of claim 7, further comprising each geometrical hole progressively narrowing from the opening to the hole termination point.

* * * * *